United States Patent
De Castro et al.

(10) Patent No.: US 11,357,248 B2
(45) Date of Patent: Jun. 14, 2022

(54) SYNTHETIC MILK COMPOSITIONS FOR INFANTS LESS THAN THREE MONTHS OLD AND FOR INFANTS AND CHILDREN MORE THAN THREE MONTHS FOR ENSURING OPTIMAL GROWTH AND PREVENTING OBESITY

(71) Applicant: NESTEC S.A., Vevey (CH)

(72) Inventors: Carlos Antonio De Castro, Geneva (CH); Cristina Cruz-Hernandez, Epalinges (CH); Frederic Destaillats, Servion (CH); Francesca Giuffrida, Mezieres (CH); Sagar Thakkar, St-Legier (CH); Rajat Mukherjee, Montreux (CH)

(73) Assignee: Societe des Produits Nestle S.A., Vevey (CH)

( * ) Notice: Subject to any disclaimer, the term of this patent is extended or adjusted under 35 U.S.C. 154(b) by 556 days.

(21) Appl. No.: 15/103,961

(22) PCT Filed: Sep. 9, 2014

(86) PCT No.: PCT/EP2014/069126
§ 371 (c)(1),
(2) Date: Jun. 13, 2016

(87) PCT Pub. No.: WO2015/086176
PCT Pub. Date: Jun. 18, 2015

(65) Prior Publication Data
US 2016/0309767 A1    Oct. 27, 2016

(30) Foreign Application Priority Data
Dec. 12, 2013   (EP) ..................................... 13196800

(51) Int. Cl.
| | | |
|---|---|---|
| *A23L 33/00* | (2016.01) | |
| *A23L 33/17* | (2016.01) | |
| *A23L 33/115* | (2016.01) | |
| *A23L 33/12* | (2016.01) | |

(52) U.S. Cl.
CPC ............ *A23L 33/40* (2016.08); *A23L 33/115* (2016.08); *A23L 33/12* (2016.08); *A23L 33/17* (2016.08); *A23L 33/30* (2016.08); *A23V 2002/00* (2013.01)

(58) Field of Classification Search
USPC .......................................................... 426/2
See application file for complete search history.

(56) References Cited

U.S. PATENT DOCUMENTS

| | | |
|---|---|---|
| 2008/0003329 A1 | 1/2008 | Rueda et al. |
| 2011/0195144 A1 | 8/2011 | Haschke et al. |
| 2011/0294757 A1* | 12/2011 | Shulman ................... A23J 7/00 514/78 |
| 2012/0121757 A1* | 5/2012 | Zwijsen ............... A61K 31/185 426/2 |
| 2013/0177667 A1* | 7/2013 | Mace ...................... A23L 1/296 426/2 |

FOREIGN PATENT DOCUMENTS

| | | |
|---|---|---|
| CN | 102984957 A | 3/2013 |
| EP | 1062873 | 12/2000 |
| RU | 2417614 C2 | 5/2011 |
| RU | 2471375 C2 | 1/2013 |
| WO | 2005051091 | 6/2005 |
| WO | 2010003878 A1 | 1/2010 |
| WO | 2010027258 | 3/2010 |
| WO | 2013153071 A2 | 10/2013 |

OTHER PUBLICATIONS

Mitoulas et al. "Variation in fat, lactose and protein in human milk over 24h and throughout the first year of lactation" British Journal of Nutrition, 2002, vol. 88, pp. 29-37.
Koletzko et al. "Can infant feeding choices modulate later obesity risk?" The American Journal of Clinical Nutrition, 2009, vol. 89, pp. 1502S-1508S.
Russian Office Action for corresponding Russian Application No. 2016128078, dated Sep. 25, 2018; (11 pages).
Kries et al., "Breast Feeding and Obesity: Cross Sectional Study", BMJ, vol. 319, Issue No. 7203, Jul. 17, 1999, pp. 147-150.
Thakkar et al., "Dynamics of Human Milk Nutrient Composition of Women from Singapore with a Special Focus on Lipids", American Journal of Human Biology, vol. 25, Issue No. 6, 2013, pp. 770-779.
Michaelsen et al., "Early Diet, Insulin-Like Growth Factor-1, Growth and Later Obesity", World Rev Nutr Diet, vol. 106, 2013, pp. 113-118.
"Early Diet, Insulin-Like Growth Factor-1, Growth and Later Obesity", Retrieved from (https://europeomc.orgiarticle/med/23428689), Feb. 2013, 1 Page.
Koletzko, "Long-Term Consequences of Early Feeding on Later Obesity Risk", Protein and Energy Requirements in Infancy and Childhood, Nestle Nutr Workshop Ser Pediatr Program, vol. 58, 2006, pp. 1-18.
Grote et al., "Protein Intake and Growth in the First 24 Months of Life", Journal of Pediatric Gastroenterology and Nutrition, vol. 51, Supplement 3, Dec. 2010, pp. S117-S119.
"Standard for Infant Formula and Formulas for Special Medical Purposes Intended for Infants", Codex Alimentarius, Codex Stan 72-1981, 17 Pages.
Koletzko et al., "Global Standard for the Composition of Infant Formula: Recommendations of an ESPGHAN Coordinated International Expert Group", Journal of Pediatric Gastroenterology and Nutrition, vol. 41, 2005, pp. 584-599.

(Continued)

*Primary Examiner* — Lien T Tran
(74) *Attorney, Agent, or Firm* — K&L Gates LLP (57) ABSTRACT

The invention concerns synthetic nutritional formulations, particularly milk based compositions, for infants and children. The compositions are especially adapted to the age of the child. They are adapted to fulfill the nutritional needs of the child, ensuring balanced growth and development and thereby reducing the risk of obesity.

9 Claims, 3 Drawing Sheets

(56) References Cited

OTHER PUBLICATIONS

Fomon, "Requirements and Recommended Dietary Intakes of Protein during Infancy", Pediatric Research, vol. 30, Issue No. 5, 1991, pp. 391-395.
Commission Directive 2006/141/EC, "Infant Formulae and Follow on Formulae and Amending Directive 1999/21/EC", Official Journal of the European Union, Dec.22, 2006, 33 pages.
"WHO Child Growth Standards based on length/height, weight and age", Acta Paediatrica, Supplement 450, 2006, pp. 76-85.
Europe Patent Office Communication of Notice of Opposition for Application No. 14761640.3-1105 / 3079770, dated Feb. 17, 2021, 40 pages.
Feng, "Common Knowledge 3: Childhood Nutriology", Heilongjiang Education Press, Jun. 2010, p. 80.
China Office Action Received for Application No. 201480066644.9, dated Apr. 15, 2020, 10 pages.
Kleinman, "Pediatric Nutrition", 7th Edition, published by People's Military Medical Press, 2015, Chapter 15, p. 254.
Shao et al., "Maternal Nutrition and Four-Season Recipes(Nutritional Guidelines & Seasonal Recipes for Pregnant and Lying-in Women)", Shanghai Medical University Press, Jul. 1992, p. 167.

* cited by examiner

SYNTHETIC MILK COMPOSITIONS FOR INFANTS LESS THAN THREE MONTHS OLD AND FOR INFANTS AND CHILDREN MORE THAN THREE MONTHS FOR ENSURING OPTIMAL GROWTH AND PREVENTING OBESITY

CROSS REFERENCE TO RELATED APPLICATIONS

The present application is a National Stage of International Application No. PCT/EP2014/069126, filed on Sep. 9, 2014, which claims priority to European Patent Application No. 13196800.0, filed Dec. 12, 2013, the entire contents of which are being incorporated herein by reference.

TECHNICAL FIELD

The invention concerns synthetic nutritional formulations, particularly milk based compositions, for infants and young children. The compositions are especially adapted to the age of the infants and young children. They are adapted to fulfill the nutritional needs of the child, ensuring balanced growth and development and thereby reducing the risk of obesity in these infants and young children.

BACKGROUND OF THE INVENTION

In general, human breast milk represents the uncontested gold standard in terms of infant nutrition. However, in some cases, breastfeeding is inadequate or unsuccessful for medical reasons or because of mother choice not to breastfeed. Infant formulae have been developed for these situations.

Infant formulae, follow-up formulae and grown-up milks which may be aimed at different age groups of 0 to 6 months, 6 months to 1 year and 1 year to 3 years respectively, are known. These infant formulae, follow-up formulae and growing-up milks aim to meet the requirements of infants and young children at the different ages. An age-tailored nutrition system for infants is described in WO 2009/068549, wherein a protein nature and content are adapted to specific age groups. The recommended World Health Organization (WHO) and Codex Alimentarius Commission guidelines for infant formulae and follow-up formulae state that the infant formulae and follow-up formulae shall not provide less than 60 kcal/100 mL and not more than 85 kcal/100 mL.

Generally, conventional infant formulae and follow-up formulae tend to provide about 67 kcal/100 mL.

However, there is generally a tendency to overfeed infants and young children. As suggested in recent literature, the composition of breast milk may contribute to the protective effects of breastfeeding against obesity in infants later in life [Ian M. P., et al. (2009) Opportunities for the Primary Prevention of Obesity during Infancy, Adv Pediatr. 56:107-133; Tounian P., (2011) Programming towards Childhood Obesity, Ann. Nutr. Metab. 58:30-41]. Usually also, the infant formulae and/or follow-up formulae dosage and caloric density do not take into consideration the complementary food eaten by infants and young children when overfeeding the infants and young children. Also the starter formulas that target all children of 0-6 months do not distinguish the nutritional needs of infants aged 0-3 months from those aged 3 to 6 months old. It is known that breast milk composition changes considerably from the first to second and third month of lactation for example.

It is known that a rapid growth of infants and young children increases a risk of obesity in later childhood or adulthood [Baird et al. (2005) Being big or growing fast: systematic review of size and growth in infancy and later obesity. B.M.J. 331(7522):929]. Infant formulas need to reduce the risk of obesity in later childhood or adulthood.

A number of studies indicate that nutrition in early postnatal life has an impact on long-term appetite regulation. For example, overfeeding rat pups results in altered appetite control with development of hyperphagia in adulthood of the rats [Davidowa, H., and Plagemann, A. (2004)]. Hypothalamic neurons of postnatally overfed, overweight rats respond differentially to corticotropin-releasing hormones [Neurosci Lett. November 16; 371(1):64-8)].

There is a need to provide a more balanced diet to infants and young children. This diet should take into account the gender of the infant or young child. It should also take into account the age of the child, specifically in months, for example 0-3, 3-6, 6-12 months etc. The diet should promote health benefits in the long term to the infants and young children.

There is a need to provide a nutritional system that enables the convenient, safe and accurate delivery of the most adequate nutrition all along the first months or years of the life of a baby.

There is need to provide a way to ensure that the best adequate individual nutritional solutions are made available to infants and their care-givers, in order to promote health benefits that may not be immediately visible but which consequences occur later in life.

There is a need to provide such cited nutritional compositions, especially during the first three years of life, that can help ensuring optimal growth and reduction of risk of health conditions later in life, such as cardiovascular diseases, diabetes, obesity, metabolic syndrome, or depressed immunity.

There is, thus, a need to provide a nutritional composition that acknowledges the gender and the specific age of the baby, while ensuring optimal growth and reduction of risk of health conditions later in life, such as cardiovascular diseases, diabetes, obesity, metabolic syndrome, or depressed immunity.

There is a need for an early-in-life nutritional intervention or control in order to deliver health benefits later-in-life.

To address these needs, the inventors have analyzed the milk from mothers to boys and from mothers to girls, at 30, 60 and 120 days post-partum in a longitudinal clinical study. Based on their results, they have designed synthetic nutritional formulas that have distinct amounts of certain nutrients depending on whether the formulation is destined for babies younger or older than three months. The compositions of the present invention have been designed to ensure balanced growth and development in the infants and young children consuming the compositions, and also to prevent obesity in infancy and later in life.

SUMMARY OF THE INVENTION

The present invention concerns synthetic nutritional formulations for infants and young children, meaning in the context of the invention, up to the age of 36 months. The compositions are especially adapted to the age of the child. The invention further relates to administration of these compositions for ensuring balanced growth in infants of up to three months old and preventing obesity in said infants and young children during infancy, childhood and later in life According to the first aspect of the invention, there is provided a set of two distinct synthetic nutritional compositions, wherein the first composition is especially adapted to the nutritional needs of an infant or young child younger than three months. The second composition is especially adapted to the nutritional needs of an infant or young child older than three months.

The first composition comprises:
a. 1.0-1.2 g/100 ml protein, and
b. 3.8-4.6 g/100 ml lipid,
and the second composition comprises:
a. 0.7-0.9 g/100 ml protein, and
b. 4.2-5.2 g/100 ml lipid.

In a preferred embodiment, the first composition may also comprise any one or a mixture of phospholipids c.-e:
c. 5.4-6.6 mg/100 ml of phosphatidylcholine,
d. 6.0-7.5 mg/100 ml of phosphatidylethanolamine, and
e. 1.0-1.2 mg/100 ml of phosphatidylinositol,
and the second composition may comprise, in addition, any one or a mixture of phospholipids c.-e.:
c. 4.4-5.4 mg/100 ml of phosphatidylcholine,
d. 7.3-8.9 mg/100 ml of phosphatidylethanolamine, and
e. 1.5-1.9 mg/100 ml of phosphatidylinositol.

The first and second compositions in the set are distinct in that they differ by at least 10% in the quantity of at least one of the common components present in the two compositions chosen among a. to e.

In a preferred embodiment, the first and second compositions are independently an infant formula in the form of a powder, liquid or concentrated liquid, or are a human milk fortifier.

In a second aspect of the invention, there is provided a synthetic nutritional composition especially adapted to the nutritional needs of an infant less than three months old. The composition comprises:
a. 1.0-1.2 g/100 ml protein, and
b. 3.8-4.6 g/100 ml lipid.

In a preferred embodiment, the first composition may also comprise any one or a mixture of phospholipids c.-e.:
c. 5.4-6.6 mg/100 ml of phosphatidylcholine,
d. 6-7.5 mg/100 ml of phosphatidylethanolamine, and
e. 1.0-1.2 mg/100 ml of phosphatidylinositol.

The synthetic nutritional compositions according to the second aspect of the invention may be an infant formula in the form of a powder, liquid or concentrated liquid, or a human milk fortifier.

In a third aspect of the invention, there is provided a synthetic nutritional composition especially adapted to the nutritional needs of an infant or young child more than three months old. The composition comprises:
a. 0.7-0.9 g/100 ml protein, and
b. 4.2-5.2 g/100 ml lipid.

In a preferred embodiment, the first composition may also comprise any one or a mixture of phospholipids c.-e.:
c. 4.4-5.4 mg/100 ml of phosphatidylcholine,
d. 7.3-8.9 mg/100 ml of phosphatidylethanolamine, and
e. 1.5-1.9 mg/100 ml of phosphatidylinositol.

The synthetic nutritional compositions according to this third aspect of the invention may be an infant formula in the form of a powder, liquid or concentrated liquid, or a human milk fortifier.

The compositions of the invention are designed to ensure balanced growth and prevent obesity in male and female infants or young children during infancy, childhood and later in life.

In one embodiment the synthetic nutritional composition or set of compositions of the invention is for infants of less than 1 year, preferably 3 months or less, and/or is for preterm and/or caesarean born infants, and/or is for infants born from a mother or parents having an history of obesity or overweight.

BRIEF DESCRIPTION OF THE FIGURES

FIGS. 1 and 2 show the results of the analysis of nutrients in the breast milk of 50 mothers in trial detailed in Example 1. Samples were taken at 30, 60 and 120 days post-partum. Quantities were measured in mg/100 ml. The measurements of milk of mothers to boys are shown with a dashed line, while the solid line shows the measurements of milk of mothers to girls. The P[gender] value relates to the differences in milk with respect to the sex of the baby. The P[age] values are differences in gender with respect to time; P[age] is a P value considering a linear model and P[age$^2$] using a quadratic model.

DETAILED DESCRIPTION

For a complete understanding of the present invention and the advantages thereof, reference is made to the following detailed description of the invention.

It should be appreciated that various embodiments of the present invention can be combined with other embodiments of the invention and are merely illustrative of the specific ways to make and use the invention and do not limit the scope of the invention when taken into consideration with the claims and the following detailed description.

In the present description, the following words are given a definition that should be taken into account when reading and interpreting the description, examples and claims.

Definitions

Infants: according to the Commission Directive 2006/141/EC of 22 Dec. 2006 on infant formulae and follow-on formulae, article 1.2 (a), the term "infants" means children under the age of 12 months.

Young Children (including young boys and young girls): according to the Commission Directives 2006/141/EC of 22 Dec. 2006 and/or 91/321/EEC of 14 May 1991 on infant formulae and follow-on formulae, article 1.2 (b), the term "young children" means children aged between one and three years.

Infant formulae: according to the Commission Directives 2006/141/EC of 22 Dec. 2006 and/or 91/321/EEC of 14 May 1991 on infant formulae and follow-on formulae, article 1.2 (c), the term "infant formulae" means foodstuffs intended for particular nutritional use by infants during the first four to six months of life and satisfying by themselves the nutritional requirements of this category of persons. It has to be understood that infants can be fed solely with infant formulas, or that the infant formula can be used by the carer as a complement of human milk. It is synonymous to the widely used expression "starter formula".

Follow-on formulae: according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

Growing-up milk: milk-based nutritional composition especially adapted to a child of between one year and three years old.

Human Milk fortifier: Nutritional composition for infants or young children intended to be added to or diluted with human milk.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

The term "prebiotic" means non-digestible carbohydrates that beneficially affect the host by selectively stimulating the growth and/or the activity of healthy bacteria such as bifidobacteria in the colon of humans [Gibson G R, Roberfroid M B. *Dietary modulation of the human colonic microbiota: introducing the concept of prebiotics*. J Nutr. 1995; 125:1401-12].

The term "probiotic" means microbial cell preparations or components of microbial cells with a beneficial effect on the health or well-being of the host [Salminen S, Ouwehand A. Benno Y. et al. "*Probiotics: how should they be defined*" Trends Food Sci. Technol. 1999:10 107-10].

An "allergy" is an allergy which has been detected by a medical doctor and which can be treated occasionally or in a more durable manner. A "food allergy" is an allergy with respect to a nutritional composition.

All percentages are by weight unless otherwise stated.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

The present inventors have carried out a major study on breast milk composition. This study involved both developing advanced analytical technologies to analyze milk samples and performing a longitudinal clinical trial with human milk sampling at 30, 60 and 120 days post-partum (see Example 1). The milk samples were quantitatively analyzed for macronutrients, lipids and phospholipids. The inventors have surprisingly found very significant differences, according to the evolution of the lactation between 0-120 days not only in energy (differences are greater than previously reported), but also in the quantities of protein, lipid and phospholipids, in particular phosphatidylcholine, phosphatidylethanolamine and phosphatidylinositol (see Table 1 and FIGS. 1 and 2).

Based upon the results of this study, the inventors have designed compositions that are especially adapted to meet the nutritional needs of infants and young children who are either younger or older than three months. To the inventor's knowledge, to date, no such age-specific formulations for infants or young children are known.

The Compositions of the Invention

The compositions of the invention are designed to meet the nutritional needs of infants and young children who are younger than three months old or between three and thirty-six months old. The compositions promote balanced growth in these infants or young children, and thereby reduce the risk of obesity during infancy, childhood and later in life.

The synthetic nutritional compositions of the invention may be an infant formula in the form of a powder, liquid or concentrated liquid. The infant formula may be based on a cow's milk, goat's milk or buffalo milk. The infant formula may be a starter formula for infants that are less than 6 months old or a follow-on formula for infants that are more than 6 months old. The composition of the invention may be a growing up milk, or a human milk fortifier. In a preferred embodiment, the composition may be cow's milk whey based infant formula. The formula may also be a hypoallergenic (HA) formula in which the cow milk proteins are (partially or extensively) hydrolysed. The formula may also be based on soy milk or a non-allergenic formula, for example one based on free amino acids.

The nutritional compositions of the invention contain specific quantities of an essential protein, depending on whether the composition is for infant of less than 3 months or infant or young children who are older than 3 months. Quantities of lipid, phosphatidylcholine, phosphatidylethanolamine, and phosphatidylinositol also vary depending on whether the composition is for infants who are younger or older than 3 months old.

All of the latter components—protein, lipids and phospholipids are known to be very important for balanced growth and development in infants and young children.

The quantities of all the nutrients expressed herein as mg/100 ml or g/100 ml reflect the amounts of nutrients present in the final liquid product, to be consumed by the infant or young child. For example, the composition may be a powdered infant formula that is diluted with water to give a final liquid product. The composition according to the invention may also be a concentrated liquid that is diluted with water to achieve the final liquid product. The composition of the invention may be a liquid product that is directly consumed by the infant or child as is. The composition according to the invention may be a human milk fortifier that is added to or diluted with human milk. In this case, the concentration of the nutrients already present in the human milk (to which the human milk fortifier is added) are to be taken as the average values for lactating mothers that are known or predicted from published clinical data.

Thus, the invention provides a synthetic nutritional composition especially adapted to the nutritional needs of an infant less than three months old. The composition comprises:

a. 1.0-1.2 g/100 ml protein, preferably 1.5-1.9 g/100 ml protein, and b. 3.8-4.6 g/100 ml lipid, preferably 4.0-4.4 g/100 ml lipid, and any one or a mixture of phospholipids c.-e.:

c. 5.4-6.6 mg/100 ml, preferably 5.6-6.4 mg/100 ml of phosphatidylcholine, d. 6-7.5 mg/100 ml, preferably 6.4-7.0 mg/100 ml of phosphatidylethanolamine, and e. 1.0-1.2 mg/100 ml, preferably 1.1 mg/100 ml of phosphatidylinositol.

Furthermore, the invention provides a synthetic nutritional composition especially adapted to the nutritional needs of an infant or young child more than three months old. The composition comprises:

a. 0.7-0.9 g/100 ml, preferably 0.75-0.85 g/100 ml protein, and
b. 4.2-5.2 g/100 ml, preferably 4.4-5 g/100 ml lipid,
and any one or a mixture of phospholipids c.-e.:
c. 4.4-5.4 mg/100 ml, preferably 4.8-5.2 mg/100 ml of phosphatidylcholine,
d. 7.3-8.9 mg/100 ml, preferably 7.5-8.2 mg/100 ml of phosphatidylethanolamine, and
e. 1.5-1.9 mg/100 ml, preferably 1.6-1.8 mg/100 ml of phosphatidylinositol.

In another aspect of the invention, there is provided a set of two distinct synthetic nutritional compositions, wherein the first composition is especially adapted to the nutritional needs of an infant or young child younger than three months. The second composition is especially adapted to the nutritional needs of an infant or young child older than three months. The first and second compositions are conditioned separately. The first and second compositions in the set are commercialized under the same marketing concept umbrella. The first and second compositions may be then conditioned separately, or group together in another outer container, or packaging. The packaging may be for example simply a layer or plastic film, a bag, box, piece of foil, or other means to keep the first and second compositions grouped together.

The set of the invention can preferably be commercialized under the same marketing concept (for example age segmentation and/or specific adaptation of nutritional compositions for infants or children at specific age).

The first composition of the set comprises:
a. 1.0-1.2 g/100 ml protein, preferably 1.5-1.9 g/100 ml protein, and
b. 3.8-4.6 g/100 ml lipid, preferably 4.0-4.4 g/100 ml lipid.

In a preferred embodiment, the first composition in the set additionally comprises any one or a mixture of phospholipids c.-e.:
c. 5.4-6.6 mg/100 ml, preferably 5.6-6.4 mg/100 ml of phosphatidylcholine,
d. 6-7.5 mg/100 ml, preferably 6.4-7.0 mg/100 ml of phosphatidylethanolamine, and
e. 1.0-1.2 mg/100 ml, preferably 1.1 mg/100 ml of phosphatidylinositol.

The second composition of the set comprises:
a. 0.7-0.9 g/100 ml, preferably 0.75-0.85 g/100 ml protein, and
b. 4.2-5.2 g/100 ml, preferably 4.4-5 g/100 ml lipid.

In a preferred embodiment, the second composition in the set additionally comprises any one or a mixture of phospholipids c.-e.:
c. 4.4-5.4 mg/100 ml, preferably 4.8-5.2 mg/100 ml of phosphatidylcholine,
d. 7.3-8.9 mg/100 ml, preferably 7.5-8.2 mg/100 ml of phosphatidylethanolamine, and
e. 1.5-1.9 mg/100 ml, preferably 1.6-1.8 mg/100 ml of phosphatidylinositol.

The set may comprise additional third, fourth and fifth etc. compositions that are especially adapted to meet the nutritional needs of infants or young children that are for example, 3-6 months old 6-9 months old or 9-12 months old. The set may also contain additional compositions that target in the same way children older than one year up to three years old.

Other Ingredients in the Compositions

Other ingredients known to the skilled person for formulating an infant formula, human milk fortifier or growing-up milk may also be present in the compositions of the invention. These may be for example fatty acids, including essential fatty acids, gangliosides and phospholipids.

The nutritional compositions of the invention may contain other ingredients which may act to enforce the technical effect of the components a.-e.

Prebiotics

The prebiotics that may be used in accordance with the present invention are not particularly limited and include all food substances that promote the growth of probiotics or health beneficial micro-organisms in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof.

In particular, the human milk oligosaccharides, for example sialylated oligosaccharides, described in WO 2012/069416 published on May 31, 2012 may be included in the composition according to the invention. The latter oligosaccharides may act in synergy with the essential fatty acids and phospholipids of the invention to promote the healthy establishment of cognitive function in the young developing infant or young child.

Probiotics may be added to the composition. All probiotic micro-organisms may be added additionally. Preferably, the probiotic may be selected for this purpose from the group consisting of *Bifidobacterium, Lactobacillus, Lactococcus, Enterococcus, Streptococcus, Kluyveromyces, Saccharomyces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM I-2618), *Bifidobacterium longum* NCC490 (CNCM I-2170), *Bifidobacterium lactis* NCC2818 (CNCM I-3446), *Bifidobacterium breve* strain A, *Lactobacillus paracasei* NCC2461 (CNCM I-2116), *Lactobacillus johnsonii* NCC533 (CNCM I-1225), *Lactobacillus rhamnosus* GG (ATCC53103), *Lactobacillus rhamnosus* NCC4007 (CG MCC 1.3724), *Enterococcus faecium* SF 68 (NCC2768; NCIMB10415), and mixtures thereof.

In one embodiment the synthetic nutritional compositions of the invention comprise probiotics active or inactivated, dead or alive, preferably in sufficient dose to be effective (e.g between $10^6$ to $10^{11}$ or between $10^7$ and $10^9$ cfu/g of composition). In one embodiment the first composition of the invention comprises a probiotic having a specific effect for that age and is different from the probiotic comprised in the second composition of the invention. In one embodiment such probiotics comprise *Bifidobacterium lactis* or *Lacto-* bacillus rhamnosus GG in the first composition and *B. longum* in the second composition (or possibly vice-versa). In one embodiment such probiotics comprise *Bifidobacterium Lactis* the first composition and *Lactobacillus Rhamnosus* in the second composition (or possibly vice-versa). The choice of probiotics is specifically adapted for the particular needs of the infants at specific age.

Vitamins, minerals and other micronutrients suitable for administration to children under the age of three may be added to the compositions of the invention.

The Compositions of the Invention Promote the Balanced Development and Prevent Obesity Later in Life The compositions according to the invention are especially adapted to promote the balanced growth in infants and young children and prevent obesity during infancy, childhood and later in life. The indicators of normative growth are defined by World Health Organization (WHO) [Acta Paediatrica, 2006; Suppl 450: 76-85]. These indicators are: length/height-for-age, weight-for-age, weight-for-length, weight-for-height, body mass, index-for-age (BMI-for-age), head circumference-for-age, arm circumference-for-age, subscapular skinfold-for-age, triceps skinfold-for-age, motor development milestones, weight velocity, length velocity and head circumference velocity. Furthermore, each indicator is available independently for male and female gender of the infant. The value of any particular indicator of an infant between 3rd and 97th percentile at a corresponding time point is considered normal and/or optimal.

Lipids in human milk provide to the infant the calories needed for growth as well as essential fatty acids and phospholipids such as phosphatidylcholine, phosphatidylethanolamine, phosphatidylserine, phosphatidylinositol and spingomelin [Jensen R G., (1999), Lipids in Human Milk, Lipids 34, 1243-1271]. The essential fatty acids include alpha-linolenic acid (ALA), an omega-3 fatty acid, and linoleic acid (LA), an omega-6 fatty acid. ALA and LA cannot be synthesized by humans and thus must be obtained from the diet.

Phosphatidylcholine (PC) and choline are critically important nutrients for the normal development of the infant [Zeisel, S. H. (1998) Choline and Phosphatidylcholine are important components of an infant's diet, in Lipids in Infant Nutrition, AOCS Press, Champaign, Ill.]. Phosphatidylcholine is the prevalent phospholipid found in cell membranes and is an important methyl donor and is involved in cholesterol homeostasis. Metabolism of PC, sphingomyelin and phosphatidylethanolamine (PE) are related, and therefore, PE is an important nutrient to support infant growth and development. In addition, dietary phospholipids such as PC, PE and phosphatidylinositol are converted into lyphosphospholipids in the gastrointestinal tract by the action of the phospholipase A2 [Chanussot F., Lécithine, metabolism et nutrition, Lavoisier (2008)].

It has been suggested that inadequate levels of proteins in formula may stimulate excess physical growth later in infancy, with persistent effects even at 2 years of age [Rolland-Cachera M. F. et al. (1995) Influence of macronutrients on adiposity development: a follow up study of nutrition and growth from 10 months to 8 years of age. Int. J. Obes. Relat. Metab. Disord. 19:573-578; Koletzko B., et al. (2009) Lower protein infant formula is associated with lower weight up to age 2 y: a randomized clinical trial. Am J Clin Nutr 2009; 89: 1836-1845]. The protein level is evolving according to the stage of lactation as demonstrated in the Example 1. Therefore, adaptation of the protein content in infant nutrition products to the nutritional needs of the growing and developing infant can be an efficient strategy to promote healthy development and avoid metabolic imbalance later in life.

Thus, in one embodiment of the invention, the synthetic nutritional composition of the invention is an infant formula (or a follow-on formula or a growing up milk or a human milk fortifier), for infant of less than 36 months, less than 24 months, less than 12 months, less than 6 months or preferably of 3 months or less. It is generally known, or at least hypothized, that early nutritional interventions can be more effective (in comparison to intervention at later stages in life) in programming the metabolic pathways of the infants to induce optimal balanced growth and thus prevent obesity during infancy and later in life According to a preferred embodiment of the invention, the compositions according to the invention are especially adapted to promote balanced growth in infants less than three months old, and to prevent obesity in these children during infancy and later in life. According to a preferred embodiment of the invention, the compositions according to the invention are especially adapted to promote balanced growth in infants and young children greater than three months old and to prevent obesity in these children during infancy, childhood and later in life.

In one embodiment of the invention the synthetic nutritional composition of the invention is an infant formula intended and/or especially designed for preterm infants and/or caesarean-born infants. It is generally known, or at least hypothized, that these subject groups are more prone to suffer from unbalanced growth (and, thus, from being obese later in life) due to the immaturity of their metabolic pathways and physiological conditions at birth. Early adaptation and control of the diet is therefore of the highest importance.

In one embodiment of the invention, the synthetic nutritional composition of the invention is an infant formula (or a follow-on formula or a growing up milk or a human milk fortifier), for infants born from mothers or parents having a history of obesity or overweight. It is generally known, or at least hypothized, that these subjects groups are more prone to suffer from unbalanced growth (and, thus, from being obese later in life), due, for example, to genetic or epigenetic predispositions. It is, therefore, critical to address such issues as early as possible during infancy by a specifically adapted diet.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention is further described with reference to the following examples. It will be appreciated that the invention as claimed is not intended to be limited in any way by these examples.

EXAMPLES

Example 1

Longitudinal Clinical Trial:

The present inventors designed a longitudinal clinical trial with 50 lactating mothers with milk sampling at 30 (visit 1), 60 (visit 2) and 120 (visit 3) days post-partum. The milk samples were quantitatively analyzed for energy and total solids.

Human milk collection: The protocol and collection of human milk was reviewed and approved by the local ethical committee of Singapore. The study took place at National University of Singapore. Volunteer mothers of term infants, who were apparently healthy and non-smokers (n=50; 31.1±3.1-year old) provided breast milk samples (approximately 30 mL; 4 weeks post-partum). Samples were collected after full expression from one breast using milk pump and while the baby was fed on the other breast. All efforts were made to collect complete feed that included fore-milk, mid-milk and hind-milk as a representation of one feed and to avoid within feed variation of lipid content. Approximately 30 mL aliquot was separated in a conical polypropylene tube for this study and the rest was fed to the infant. Samples collected for research were stored at −80° C. until analyses.

Macronutrient Analysis by Mid-Infrared (MIR) Assay: The MIR analyses were performed with the Human Milk Analyzer (HMA, Miris, Sweden). The HMA is based on a semisolid MIR transmission spectroscopy, designed specifically for determination of the macronutrient composition of human milk. The use of the machine was according to manufacturer's instructions. Briefly 1 mL of previously warmed milk sample (up to 40° C. in water bath) was sonicated for 1 min before manual injection to the milk inlet. The analysis was conducted within next minute before the milk was retrieved and the inlet washed with de-ionized water. The cell was also washed with supplied detergent every 5 sample injections. Also every 10 samples an in-house control as well as calibrating standard provided by Miris were ran for quality control purposes.

Fatty Acid Analysis: Fatty acid methyl esters (FAMEs) were prepared using HCl/Methanol (3N) as a catalyst. The methylation procedure was as follows: In a 15 mL test tube equipped with Teflon-lined screw caps, 250 µL of human milk was added followed by 300 µL of internal standard FAME 11:0 and 300 µL of internal standard TAG 13:0, 2 mL of methanol, 2 mL of methanol/HCL (3N) and 1 mL of n-hexane. Test tubes were firmly capped, shaken vigorously and heated at 100° C. for 60 min, with occasional additional shaking. Care was taken to fit the cap tightly with cap liner to avoid leaks when tubes are heated at 100° C. After cooling down to room temperature, 2 mL water is added and shaken vigorously for centrifugation at 1200 g for 5 min followed by the transfer of the upper phase (hexane) into GC vials. For optimal GLC separation, the use of a long (100 m), highly polar capillary column is recommended. These columns allow accurate separation of FAME, including the cis and trans isomers. GLC analyses were performed according to standard conditions known to the skilled person. A 7890A gas-chromatograph with a 7693 autosampler with preparative station module (Agilent Technologies, Palo Alto, Calif.) equipped with a fused-silica CP-Sil 88 capillary column (100% cyanopropylpolysiloxane; 100 m, 0.25 mm id, 0.25 µm film thickness; Agilent, Palo Alto, Calif.) was used with a split injector (1:25 ratio) heated at 250° C. and a flame-ionization detector operated at 300° C. The oven temperature programming used was 60° C. isothermal for 5 min, increased to 165° C. at 15° C./min, isothermal for 1 min at this temperature, and then increased to 195° C. at 2° C./min and held isothermal for 14 min and then increased to 215° C. at 5° C./min and held isothermal for 8 min at 215° C. Hydrogen was used as carrier gas under constant flow mode at 1.5 mL/min.

Phospholipid Analysis: Phospholipid families were separated by normal-phase high-performance liquid chromatography using 2 Nucleosil 50-5, 250×3 mm, 5µ (Macherey-Nagel, Easton, USA) equipped with pre-column Nucleosil 50-5, 8×3 mm, 5µ (Macherey-Nagel, Easton, USA). The chromatography system consisted of an Agilent 1200 module (Agilent Technologies, Basel, Switzerland) and an in-line PL-ELS 1000 evaporative light scattering detector (Polymer Laboratories, Shropshire England). All chromatography was performed at 55° C. Solvent A was composed of ammonium formiate 3 g/L and solvent B of acetonitrile/methanol (100/3 v/v). Gradient conditions for phospholipid analysis were as follows: time=0 min 1% solvent A; time=19 min 30% solvent A; time=21 min 30% solvent A; time=24 min 1% solvent A; flow rate was 1 mL/min. Data were collected and processed using Agilent Chem. Station software.

Figure 1A:
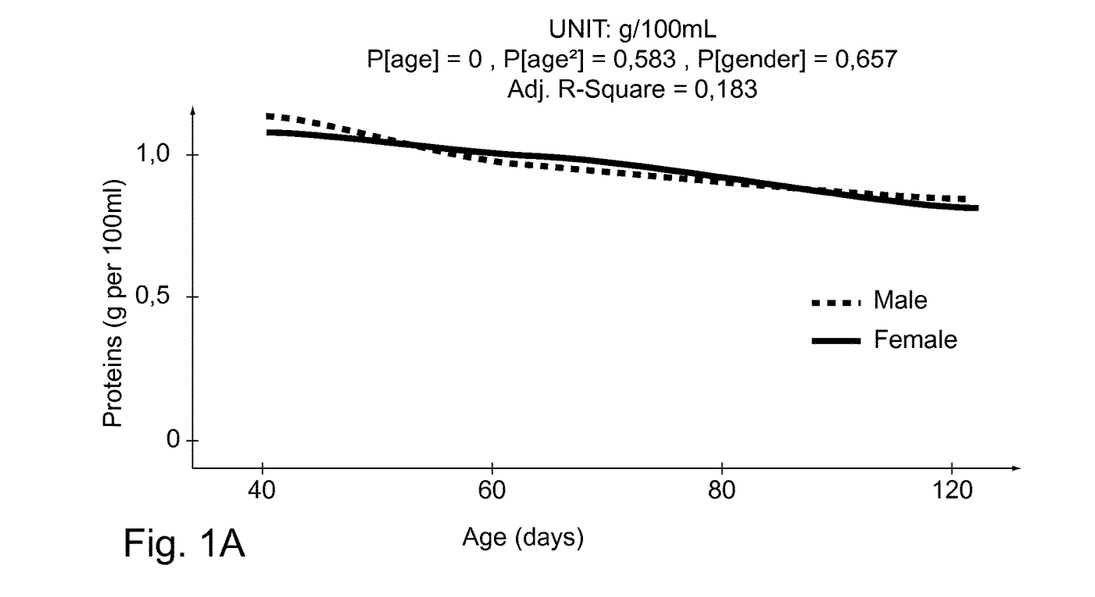
FIG. 1A shows proteins.
Figure 1B:
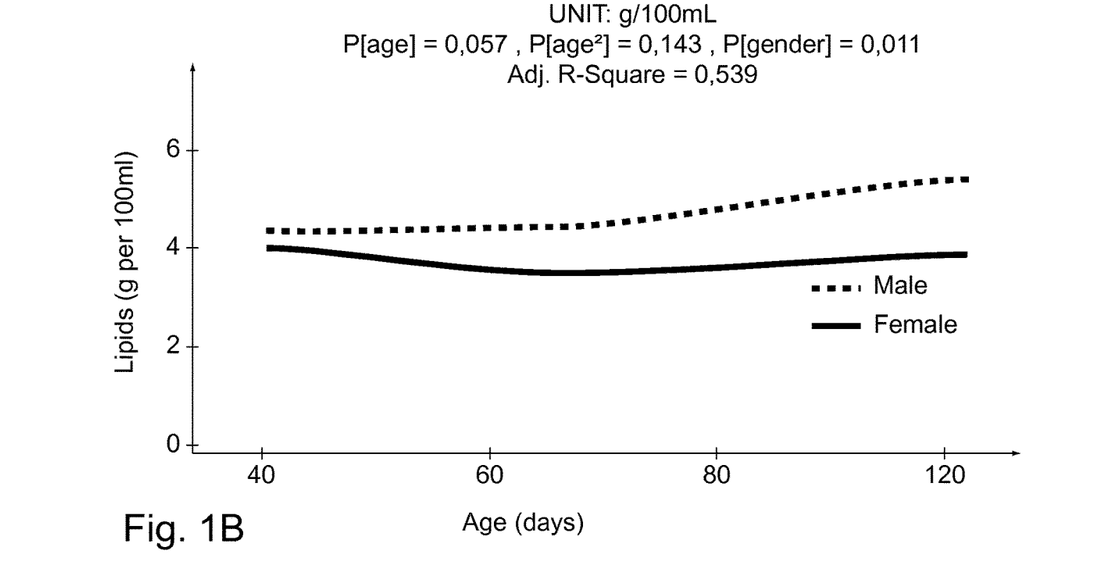
FIG. 1B shows lipids.
Figure 2A:
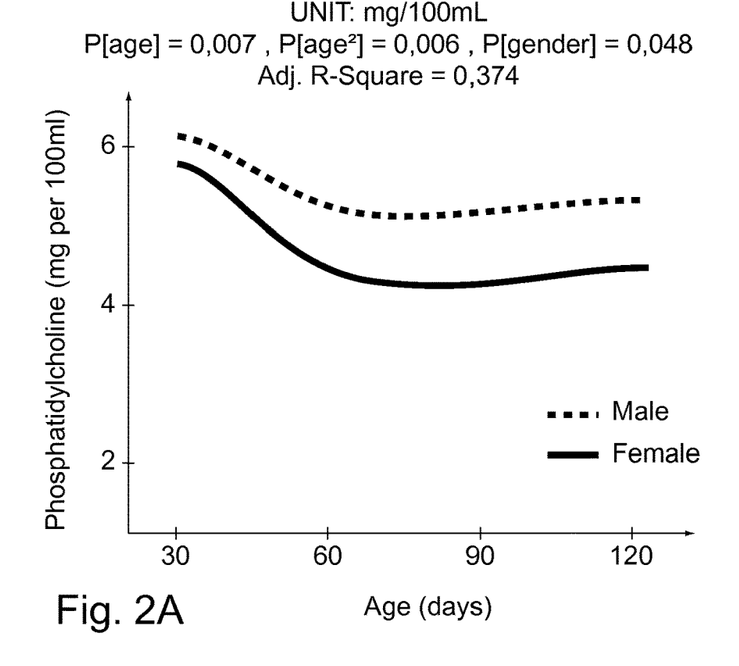
FIG. 2A shows phosphatidylcholine.
Figure 2B:
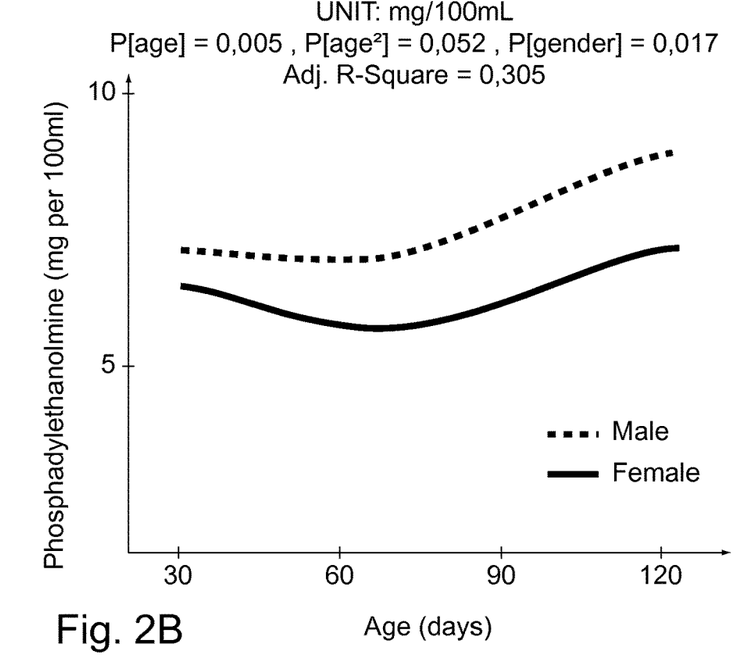
FIG. 2B shows phosphatidylethanolamine and FIG. 2C shows phosphatidylinositol.
Figure 2C:
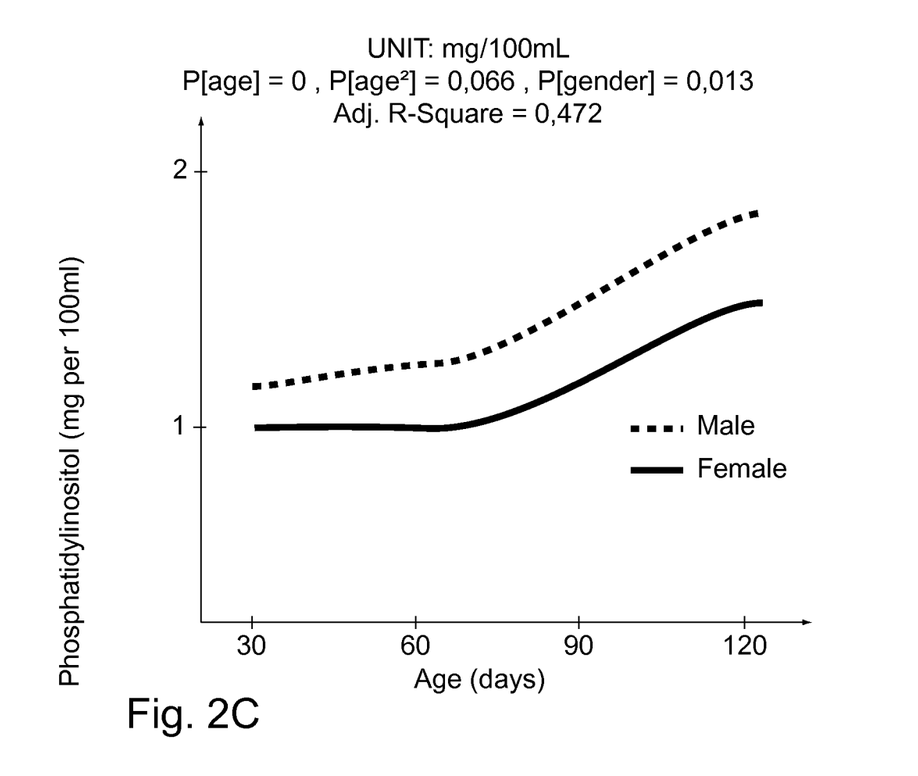

Statistical Analysis:

Data collection points are 1, 2 and 4 months after infants' birth. Table 1 shows the Min, Mean, SD and Max for each unit of measurement Statistical models fitted to the raw data are shown in FIGS. 1-3. Longitudinal analysis was carried out using linear mixed models. The figures also show the sequential effect of each of the terms age, $age^2$, gender and age-gender interactions in this particular order in terms of the P-value for the corresponding F-test. Thus, the P[age] is a P value considering a linear model and P[$age^2$] corresponds to a quadratic one. The appropriate model is chosen according to whether the trajectory is linear (P[age]) or curved (P[$age^2$]).

Adjusted R-squares were computed to obtain the degree of variability that is explained by the statistical models used.

Analysis was carried out using the following mixed-effects linear model:

$$Conc:=Age+Age^2+Gender+Age\_Gender+(Age^2)\_Gender+Random\ Effects:$$

Random effects are subject specific terms to model the underlying correlation between repeat measures.

TABLE 1

Longitudinal evolution of the concentration of proteins, lipids, phosphatidylcholine, phosphatidylethanolamine and phosphatidylinositol in human milk (N = 50)

| Nutrient | Visit | Min | Mean | SD | max |
|---|---|---|---|---|---|
| Proteins (g per 100 mL) | V1 | 0.3 | 1.1 | 0.2 | 1.5 |
|  | V2 | 0.4 | 1.0 | 0.2 | 1.6 |
|  | V3 | 0.0 | 0.8 | 0.3 | 2.0 |
| Lipids (g per 100 mL) | V1 | 2.5 | 4.2 | 0.9 | 6.2 |
|  | V2 | 0.7 | 4.0 | 2.0 | 11.9 |
|  | V3 | 0.4 | 4.7 | 2.1 | 10.5 |
| Phosphatidylcholine (mg per 100 mL) | V1 | 3.3 | 6.0 | 1.3 | 9.2 |
|  | V2 | 1.6 | 4.8 | 2.1 | 11.9 |
|  | V3 | 2.0 | 4.9 | 1.9 | 10.2 |
| Phosphatidylethanolamine (mg per 100 mL) | V1 | 3.2 | 6.8 | 1.9 | 11.1 |
|  | V2 | 2.4 | 6.4 | 3.1 | 18.3 |
|  | V3 | 2.7 | 8.1 | 3.1 | 15.4 |
| Phosphatidylinositol (mg per 100 mL) | V1 | 0.5 | 1.1 | 0.4 | 2.3 |
|  | V2 | 0.4 | 1.1 | 0.6 | 2.7 |
|  | V3 | 0.6 | 1.7 | 0.7 | 3.9 |

Example 2

An example of a starter infant formula for infant children up to the age of three months is given below. The protein source is a conventional mix of whey protein and casein.

| Nutrient | per 100 kcal | per liter |
| --- | --- | --- |
| Energy (kcal) | 100 | 659.2 |
| Protein (g) | 1.67 | 11.02 |
| Fat (g) | 6.28 | 41.72 |
| Linoleic acid (g) | 0.85 | 5.66 |
| α-Linolenic acid (mg) | 60 | 400.4 |
| Lactose (g) | 9.7 | 62.76 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1 |
| Niacin (mg) | 1 | 6.7 |
| Vitamin B6 (mg) | 0.075 | 0.5 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Phosphatidylcholine (mg) | 9.14 | 59.7 |
| Phosphatidylethanolamine (mg) | 10.33 | 67.6 |
| Phosphatidylinositol (mg) | 1.66 | 10.7 |

Example 3

An example of a starter infant formula for infant children older than three months is given below. The protein source is a conventional mix of whey protein and casein.

| Nutrient | per 100 kcal | per liter |
| --- | --- | --- |
| Energy (kcal) | 100 | 702.43 |
| Protein (g) | 1.29 | 8.31 |
| Fat (g) | 6.31 | 46.47 |
| Linoleic acid (g) | 0.87 | 6.28 |
| α-Linolenic acid (mg) | 50 | 380.5 |
| Lactose (g) | 9.48 | 64.45 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1 |
| Niacin (mg) | 1 | 6.7 |
| Vitamin B6 (mg) | 0.075 | 0.5 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Phosphatidylcholine (mg) | 6.89 | 49.4 |
| Phosphatidylethanolamine (mg) | 11.28 | 80.8 |
| Phosphatidylinositol (mg) | 2.34 | 16.7 |

The invention claimed is:

1. A method for promoting balanced growth in an infant up to three months old and reducing a risk of obesity in the infant during infancy and later in life, the method comprising administering to the infant a synthetic nutritional composition that is a foodstuff comprising:
1.0-1.2 g/100 ml protein,
3.8-4.6 g/100 ml lipid, and
at least one phospholipid selected from the group consisting of:
5.4-6.6 mg/100 ml of phosphatidylcholine,
6-7.5 mg/100 ml of phosphatidylethanolamine, and
1.0-1.2 mg/100 ml of phosphatidylinositol.

2. The method of claim 1, wherein the balanced growth is defined according to indicators defined by World Health Organization (WHO).

3. The method of claim 1, wherein the at least one phospholipid comprises:
5.4-6.6 mg/100 ml of phosphatidylcholine,
6-7.5 mg/100 ml of phosphatidylethanolamine, and
1.0-1.2 mg/100 ml of phosphatidylinositol.

4. The method of claim 1, wherein the synthetic nutritional composition comprises whey protein, casein, lactose, vitamins and minerals.

5. The method of claim 1, wherein the infant is a preterm infant and/or a caesarean-born infant.

6. The method of claim 1, wherein the infant was born from a mother having obesity or overweight.

7. The method of claim 4, wherein the at least one phospholipid comprises:
5.4-6.6 mg/100 ml of phosphatidylcholine,
6-7.5 mg/100 ml of phosphatidylethanolamine, and
1.0-1.2 mg/100 ml of phosphatidylinositol.

8. The method of claim 5, wherein the at least one phospholipid comprises:
5.4-6.6 mg/100 ml of phosphatidylcholine,
6-7.5 mg/100 ml of phosphatidylethanolamine, and
1.0-1.2 mg/100 ml of phosphatidylinositol.

9. The method of claim 6, wherein the at least one phospholipid comprises:
5.4-6.6 mg/100 ml of phosphatidylcholine,
6-7.5 mg/100 ml of phosphatidylethanolamine, and
1.0-1.2 mg/100 ml of phosphatidylinositol.

* * * * *